United States Patent
Zhuang et al.

(10) Patent No.: US 7,214,778 B2
(45) Date of Patent: May 8, 2007

(54) **GLYCOPROTEIN WITH ANTIDIABETIC, ANTIHYPERTENSIVE, ANTIOBESITY AND ANTIHYPERLIPIDEMIC EFFECTS FROM *GRIFOLA FRONDOSA*, AND A METHOD FOR PREPARING SAME**

(75) Inventors: Cun Zhuang, Fort Lee, NJ (US); Hirokazu Kawagishi, Shizuoka (JP); Harry G. Preuss, Washington, DC (US)

(73) Assignee: Masaki Shirota, Paramus, NJ (US)

( * ) Notice: Subject to any disclaimer, the term of this patent is extended or adjusted under 35 U.S.C. 154(b) by 454 days.

(21) Appl. No.: 10/762,927

(22) Filed: Jan. 22, 2004

(65) Prior Publication Data

US 2005/0014683 A1 Jan. 20, 2005

Related U.S. Application Data

(60) Provisional application No. 60/488,337, filed on Jul. 18, 2003.

(51) Int. Cl.
*C07K 1/00* (2006.01)
*A61K 38/16* (2006.01)
*A23K 1/00* (2006.01)

(52) U.S. Cl. .................. 530/395; 530/350; 530/412; 530/414; 530/417; 530/418; 530/424; 514/8; 514/866; 514/909; 426/49; 426/615; 426/655

(58) Field of Classification Search ............... 530/395, 530/350, 412, 414, 417, 418, 424; 514/8, 514/866, 909; 426/49, 615, 655
See application file for complete search history.

(56) References Cited

U.S. PATENT DOCUMENTS 5,854,404 A 12/1998 Nanba et al.

OTHER PUBLICATIONS

Kusano et al., "Isolation of Antidiabetic Components from White-Skinned Sweet Potato (*Ipomoea batatas* L)", Biosci. Biotechnol. Biochem., vol. 65, No. 1, pp. 109-114, 2001.*

Keiko Kubo, Hisao Aoki, and Hiroaki Nanba. "Anti-diabetic Activity Present in the Fruit Body of *Grifola frondosa* (Maitake). I", Biol. Pharm. Bull., vol. 17, No. 8, 1994, pp. 1106-1110.

Hirotada Kurushima, Noriko Kodama and Hiroaki Nanba. "Activities of polysaccharides obtained from *Grifola frondosa* on insulin-dependent diabetes mellitus induced by streptozotocin in mice", Mycoscience, vol. 41, 2000, pp. 473-480.

Keiko Kubo and Hitoaki Nanba. "Anti-Diabetic Mechanism of Maitake (*Grifola frondose*)", Penn. State Univ., 1996, pp. 215-221.

Manohar V., Talpur N.A., Echard B.W. Lieberman S. and Preuss H.G. "Effects of a water-soluble extract of maitake mushroom on circulating glucose/insulin concentrations in KK mice", Diabetes, Obesity and Metabolism, vol. 4, 2002, pp. 43-48.

Talpur N.A., Echard B.W., Fan A.Y., Jaffari O., Bagchi D. and Preuss H.G. "Antihypertensive and metabolic effects of whole Maitake mushroom powder and its fractions in two rat strains", Molecular and Cellular Biochemistry, vol. 237, 2002, pp. 129-136.

\* cited by examiner

*Primary Examiner*—Jon Weber
*Assistant Examiner*—Abdel A. Mohamed
(74) *Attorney, Agent, or Firm*—Simpson & Simpson, PLLC

(57) ABSTRACT

A glycoprotein extracted from the fruiting body of *Grifola frondosa* is demonstrated to have antidiabetic, antihypertensive, antiobesity and antihyperlipidemic effects, and has great potential as an active component for pharmaceuticals, dietary supplements or health food preparations to treat and/or prevent the above diseases. This invention is to provide the glycoprotein and its preparation method.

37 Claims, 3 Drawing Sheets

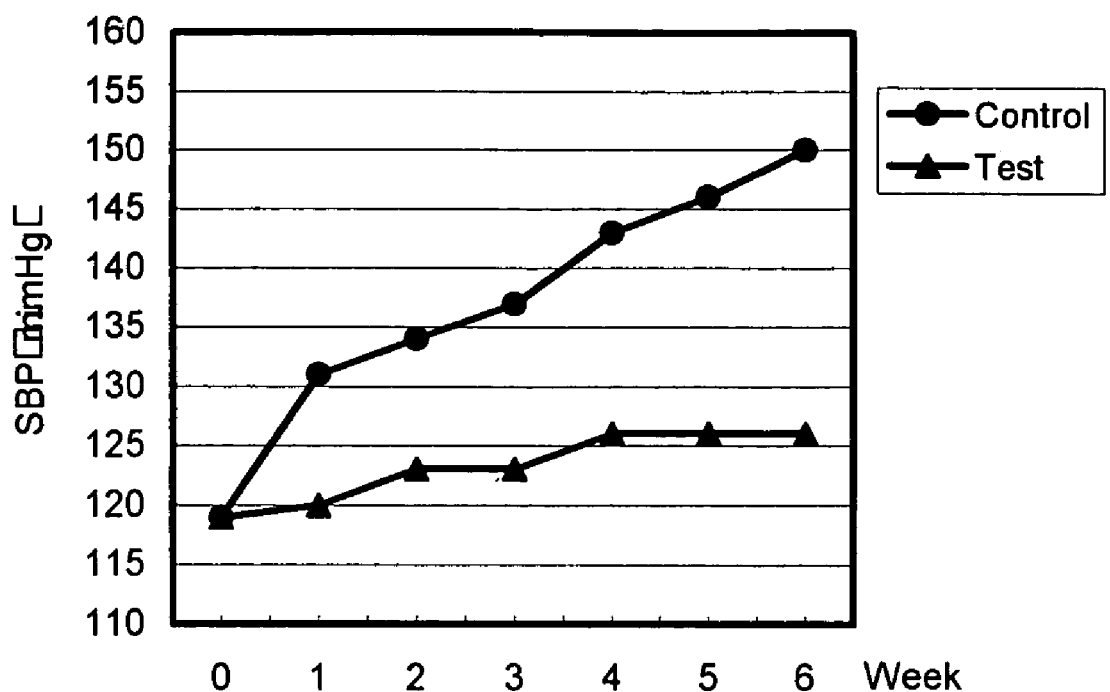
Figure 1. Antihypertensive Effect on the Younger ZFR

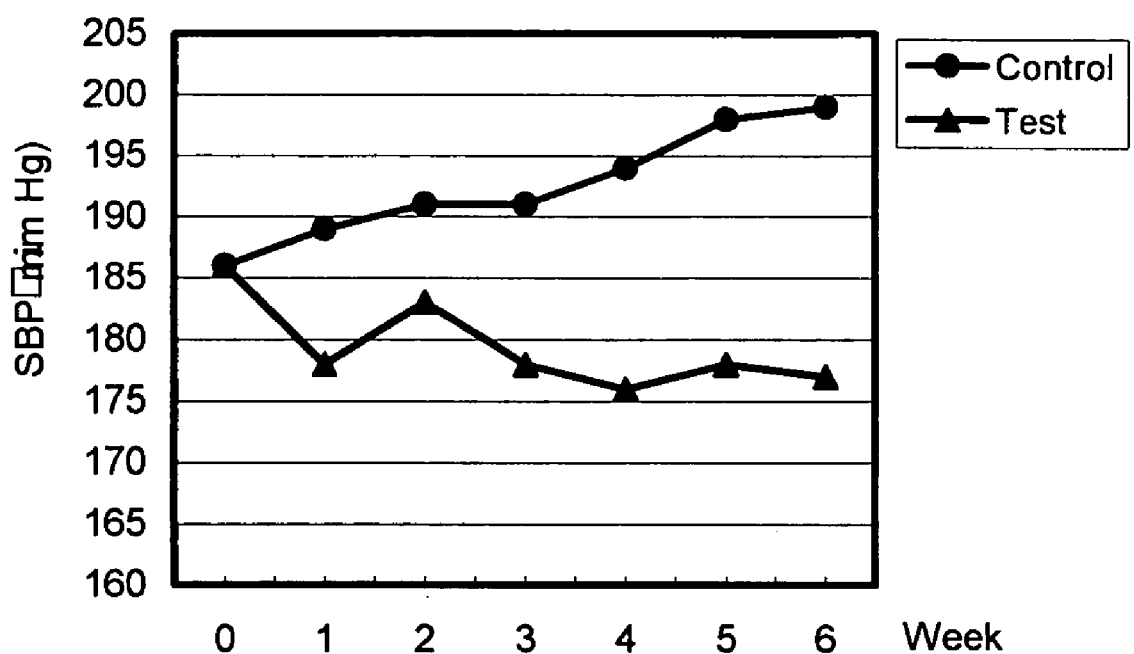
Figure 2. Antihypertensive Effect on the Older ZFR

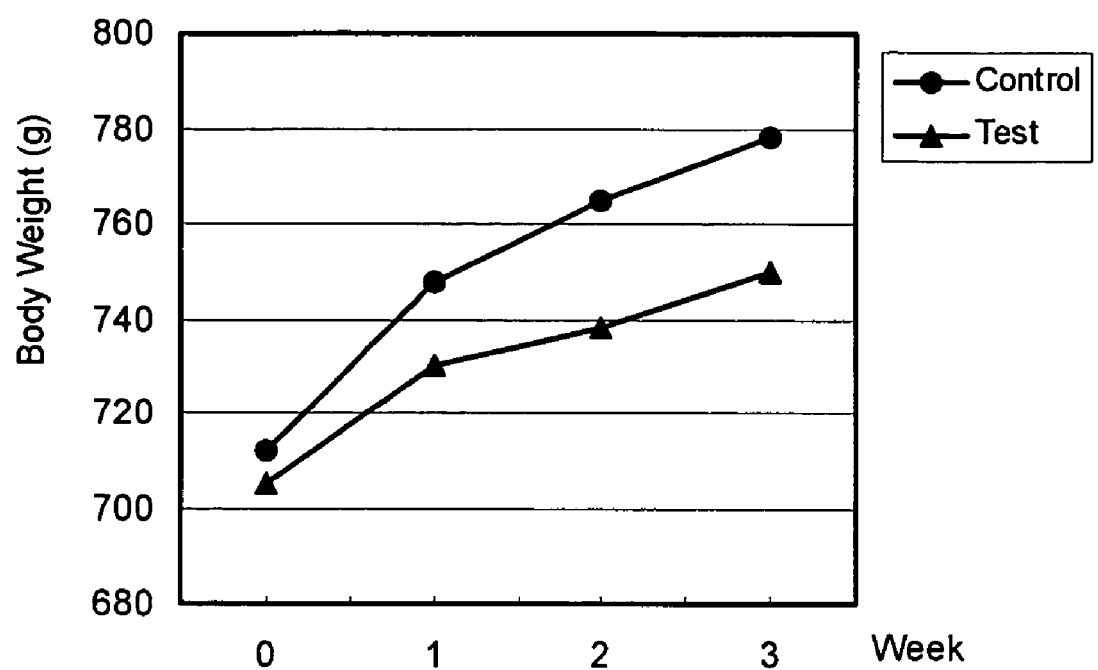
Figure 3. Antiobesity Effect on ZFR

GLYCOPROTEIN WITH ANTIDIABETIC, ANTIHYPERTENSIVE, ANTIOBESITY AND ANTIHYPERLIPIDEMIC EFFECTS FROM *GRIFOLA FRONDOSA*, AND A METHOD FOR PREPARING SAME

CROSS REFERENCE TO RELATED APPLICATIONS

This application claims the benefit of U.S. Provisional Application No. 60/488,337 filed Jul. 18, 2003 and which is incorporated by reference herein.

FIELD OF INVENTION

The present invention relates to the field of therapeutic pharmaceutical compounds derived from natural products. More specifically, the present invention relates to a glycoprotein with antidiabetic, antihypertensive, antiobesity and antihyperlipidemic effects recovered from the fruiting body of *Grifola frondosa*, and a method for preparing the glycoprotein.

BACKGROUND OF THE INVENTION

Over the past several years, much has been written concerning the relatively high level of cardiovascular disease and diabetes and their related symptoms in Western countries. Recently, several of the symptoms have been grouped into a cluster called Metabolic Syndrome X (Syndrome X). This cluster of symptoms includes medical conditions such as insulin resistance, which can lead to Type II diabetes, hypertension, low HDL cholesterol, high LDL cholesterol, high triglyceride levels, high blood insulin, and obesity.

It appears likely that the basis of Syndrome X is insulin resistance. Insulin is required by the cells of the body to enable them to absorb glucose. Insulin resistance may be defined as the reduced capacity of the body to absorb glucose due to a reduced sensitivity to insulin secreted by the body. In other words, even though insulin is produced by the pancreas in response to an increase in blood glucose, the body is not able to absorb the increased glucose. This can lead to an even greater output of insulin as blood glucose continues to increase, often leading to the gradual inactivation of the beta cells responsible for insulin production and the onset of a diabetic condition. However, even if diabetes does not occur, the insulin resistance condition results in increased blood triglycerides due to the metabolizing of fat to replace sugar as an energy source for the body. This can lead to hypertension.

While diet and exercise are thought to help alleviate insulin resistance and thus Syndrome X, currently, there are few pharmaceutical compounds that reduce insulin resistance in the body. Because it is often difficult to maintain an adequate diet and exercise program, and because such a program may not always work, a need exists for a safe pharmaceutical compound that helps to reduce insulin resistance and its resultant symptoms.

SUMMARY OF THE INVENTION

The present invention broadly comprises a water soluble glycoprotein extracted from the mushroom *Grifola frondosa* (maitake) having a protein to saccharide ratio ranging from about 75:25 to about 90:10. The present invention also includes a method of extracting the water soluble glycoprotein from the mushroom *Grifola frondosa* in which the residue of an ethanol extraction of the fruiting body of the mushroom *Grifola frondosa* is further extracted with hot water, ethanol is added to the water soluble fraction to a final concentration of 50–75%, the resulting precipitate and floating matter is removed and the supernatant is separated to collect a fraction with average molecular weight of 14,000 or more. This fraction is further purified to obtain the glycoprotein with average molecular weight of 20,000.

The present invention also includes an antidiabetic, antihypertensive, antiobesity and antihyperlipidemic product whose main ingredient includes the water soluble glycoprotein An object of the invention is to provide a compound having antidiabetic, antihypertensive, antiobesity and antihyperlipidemic activities.

A second object of the invention is to identify the chemical composition of the active compound.

An additional object of the invention is to provide a process of extracting the water soluble glycoprotein that has a high measure of safety.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which:

FIG. 1 is a graph depicting the antihypertensive effect of the glycoprotein of the present invention on younger Zucker Fatty Rats (ZFR).

FIG. 2 is a graph depicting the antihypertensive effect of the glycoprotein of the present invention on older ZFR rats.

FIG. 3 is a graph depicting the effect of the glycoprotein of the present invention on the body weight of ZFR.

DETAILED DESCRIPTION OF THE INVENTION

While the present invention has been described with respect to what is presently considered to be the preferred embodiments, it is understood that the invention is not limited to the disclosed embodiments. The present invention is intended to cover various modifications and equivalent arrangements included within the spirit and scope of the appended claims.

The glycoprotein of the present invention is obtained by a combined ethanol-water extraction procedure described in Example 1 below in which ground or pulverized fruiting body of the mushroom *Grifola frondosa*, a member of the Polyporaceae family, is first extracted with ethanol, after which the resulting residue is exposed to a hot water extraction. Ethanol is added to the obtained water-soluble extract to a final concentration of 50–75% and the resulting precipitate and floating matter are removed. The supernatant liquid is fractionated and further purified to obtain the resulting compound described in Example 2 below. Hereinafter, the resulting compound is identified as the glycoprotein.

EXAMPLE 1

The method of obtaining the glycoprotein of the present invention is described as follows:

1,000 g of the dried fruiting body of *Grifola frondosa* was extracted with 5 L of ethanol at room temperature for 2–3 hours to remove ethanol-soluble compounds. The residue was extracted with 5 L of deionized water at 100–120° C. for 2 hours. In a preferred embodiment of the method of the present invention, the residue is extracted with 5 L of deionized water at 120° C. at a pressure of about 1.2 atmospheres. After the resulting hot water extract is concentrated into half of the original volume, ethanol is added to the concentrated extract to a final ethanol concentration of 50–75% by volume. After the liquid was left standing at 4–10° C. for 8–12 hours, the precipitate and floating matter in the liquid, on the liquid, and/or adhering to the vessel wall are removed. In a preferred embodiment, the precipitate and/or floating matter may be removed by a skimming system or by a pipetting system. In a more preferred embodiment, the precipitate and/or floating matter may be removed by centrifugation. In a preferred embodiment of the method of the present invention, the ethanol solution is left at 40° C. for 8–12 hours. The supernatant liquid is subjected to separation, and the fraction of molecular weight over 14,000 daltons is collected. In a preferred embodiment, the supernatant liquid may be separated using ultrafiltration or filtered centrifugation, such as with a Centricon by Millipore. In a more preferred embodiment, the supernatant liquid may be separated using dialysis. This fraction is purified to yield approximately 21 g (dried weight) of brown substance. In a preferred embodiment, the over 14,000 daltons molecular weight fraction may be purified using electrophoresis. In a more preferred embodiment, the over 14,000 daltons molecular weight fraction may be purified using gel filtration chromatography on a Sephacryl 300 S column. This substance was positive when analyzed with the Biuret reaction and the Fehling reaction tests, and was identified as a glycoprotein by quantitative analysis using the Bradford method and the Phenol-sulfuric acid method, which methods are well known to those skilled in the art.

EXAMPLE 2

The glycoprotein obtained above in Example 1 was analyzed to examine its characteristics.

The chemical composition of the glycoprotein was determined using Nuclear Magnetic Resonance (NMR) methods well known in the art. The glycoprotein was determined to have a ratio of protein to saccharide ranging from about 75:25 to about 90:10. The results are shown in Table 1. Each of Samples 1–4 comprises material collected from separate fractionation procedures as described above.

TABLE 1

Ratio of Protein and Saccharide of Glycoprotein

| Sample | Protein | Saccharide |
|--------|---------|------------|
| 1 | 83.8% | 16.2% |
| 2 | 75.8% | 24.2% |
| 3 | 86.7% | 13.3% |
| 4 | 79.8% | 20.2% |

The amino acid composition of the protein portion of the glycoprotein was determined using a Hitachi L8500 A Amino Acid Analyzer. The protein was found to have the following amino acids: Asparagine, Glutamine, Serine, Threonine, Glycine, Alanine, Valine, Cysteine, Methionine, Isoleucine, Leucine, Tyrosine, Phenylalanine, Lysine, Histidine, Arginine, and Proline.

The saccharide portion of the glycoprotein was determined using HPLC, and found to have Galactose, Mannose, Glucose, N-acetylglucosamine, and Fucose.

Molecular weight was determined using SDS-PAGE. The average molecular weight was found to be about 20,000 daltons.

The following examples describe several experiments performed in order to investigate the biological activities of the glycoprotein.

EXAMPLE 3

Two groups of Zucker Fatty Rats (ZFR), a rat model of insulin resistance and obesity, approximately eight weeks of age, were administered with either distilled water as a control or the glycoprotein in distilled water at a dose of 15 mg/kg/day. Each group consisted of six rats. On day 35, four hours after food was removed, blood was drawn for the analyses of blood chemistries. SBP (Systolic Blood Pressure) was measured weekly throughout the experiment.

As shown in FIG. 1, the SBP of the control group fed with distilled water only rose steadily over six weeks from an average of 119 mm Hg to an average of 150 mm Hg. In contrast, the test group administered with the glycoprotein increased from an average of 119 mm Hg to an average of 126 mm Hg. It is clear that the glycoprotein has a significant antihypertensive effect.

The analyses of blood chemistries were performed and the result was shown in Table 2. The test group administered with the glycoprotein had lower average values of circulating glucose, cholesterol and triglyceride concentrations compared to those in control on day 35 of the experiment.

TABLE 2

Antidiabetic and Antihyperlipidemic Effects on ZFR rats.

| Group | Glucose (mg/dl) | Total Cholesterol (mg/dl) | Triglyceride (mg/dl) |
|-------|-----------------|---------------------------|----------------------|
| Control | 159 ± 6.5 | 133 ± 12.9 | 576 ± 89 |
| Test | 140 ± 4.8 | 128 ± 7.8 | 453 ± 93 |

Analyzed on day 35 after glycoprotein administered

EXAMPLE 4

In the above experiment, the glycoprotein was demonstrated to have a significant antihypertensive effect on the younger ZFR rats. In order to investigate if the glycoprotein has the same effect on the older ZFR rats, 70–75 week old ZFR rats (in the last one third of their life-span) were used in the experiment. The results shown in FIG. 2 showed that the SBP of the older ZFR rats administered with the glycoprotein in distilled water at a dose of 24 mg/kg/day were significantly lower than that of the control group during the six weeks experiment.

In the 70–75 week old ZFR rats, the blood glucose of the test group on day 35 of the experiment showed 151+/−11 mg/dl compared to 218+/−18 mg/dl for the control group.

EXAMPLE 5

Approximately fifteen week-old ZFR rats with fast-growing body weight were used in the experiment. The glycoprotein in distilled water was administered to the test group at a dose of 24 mg/kg/day, while the control group was administered distilled water as a control. The body weight was measured weekly throughout the three-week experiment period. FIG. 3 showed that the increase of body weight in the test group was significantly smaller than the increase in body weight of the control group.

EXAMPLE 6

Five-week old male and female mice of the ICR strain were used in the experiment. Ten each of male and female mice were allocated to each group, and the mice were not fed for about four hours prior to the administration of the appropriate test mixture and then each was weighed. To the mice of the test group, the glycoprotein dissolved in pure water was administered orally with a stomach tube at a dose of 2,000 mg/kg. To the control group, pure water alone was administered at a volume of 0.7 mL each in males and 0.6 mL each in females in the same manner as in the test group. Clinical observations were made during 14 days of the experiment period, and at the end of the experimental period all mice were sacrificed for internal organ examination.

Throughout the experimental period, no animal deaths, no abnormalities in general physical condition, and no significant difference in the mean body weight were observed in either males or females after the administration. Also, no note-worthy changes were found in any organ of either males or females in any of the internal examinations. Consequently, it was concluded that the LD50 of the glycoprotein was higher than 2,000 mg/kg at single dose.

EFFECT OF THE INVENTION

It is obvious that the glycoprotein has significant antidiabetic, antihypertensive, antiobesity and antihyperlipidemic effects on ZFR rats when administered orally. Therefore, the glycoprotein may be useful for prevention and improvement of Syndrome X or Visceral Fat Syndrome, and for prevention and treatment of diabetes, hypertension, obesity and hyperlipidemia.

The glycoprotein of this invention is totally different from proteoglucans or proteins as described in prior patents and publications, and is nontoxic and safe in use. The glycoprotein is able to be used as an active component for pharmaceutical and/or dietary supplement products in tablet, capsule, tincture, granule and drink forms. For tablet manufacture, the glycoprotein may be combined with excipients such as, but not limited to, dicalcium phosphate, sucrose fatty acid ester, microcrystalline cellulose, lactose, silica or other inactive fillers and binders well known to those skilled in the art. For soft capsules, the glycoprotein may be combined with excipients, such as, but not limited to, soybean oil, while in liquid form, carriers including, but not limited to, glycerine may be used as inactive carriers of the glycoprotein. Methods of manufacturing all the above product configurations are known to those skilled in the art.

Also, it should be noted that a variety of dietary supplement products can be formulated by combining the glycoprotein with other natural products such as, but not limited to chromium, vanadium, alpha-lipoic acid, bitter melon, cinnamon, olive oil, Gymnema sylvestre, fenugreek, ginseng, garlic, nopal cactus, aloe, bilberry, banaba leaf as well as other medicinal mushrooms, including, but not limited to Reishi, Shiitake, Tremella and Cordyceps.

Further, the glycoprotein can be used as an additive for health foods, functional foods and other general foods that may be targeted to have health benefits claimed under this invention. This glycoprotein can be used not only for health foods designed for humans but also for animal feed.

The method of this invention is safer and easier for use in industry compared to those described in the prior art and appears to possess a more stable yield rate.

Thus it is seen that the objects of the invention are efficiently obtained, although changes and modifications to the invention should be readily apparent to those having ordinary skill in the art, which changes would not depart from the spirit and scope of the invention as claimed.

We claim:

1. A method for preparing a bioactive glycoprotein fraction comprising in order the steps of:
   extracting the fruiting body of Grifola frondosa with ethanol at room temperature, and removing the ethanol extract;
   extracting the resulting residue with hot water at 100–120° C., and adding ethanol to the hot water extract to a final ethanol concentration of 50–75% by volume;
   removing the resulting precipitate and floating matter after standing at 40°–10° C. for 8–12 hours, wherein said floating matter is on the liquid or in the liquid or adhering matter to vessel wall;
   collecting a fraction molecular weight equal to or greater than 14,000 daltons from the supernatant; and
   wherein the bioactive glycoprotein fraction comprises a bioactive glycoprotein having a protein to saccharide ratio ranging from about 75:25 to about 90:10.

2. The method for preparing a bioactive glycoprotein fraction as recited in claim 1 wherein said collection of a fraction with a molecular weight equal up or greater than 14,000 daltons is performed by dialysis.

3. The method for preparing a bioactive glycoprotein fraction as recited in claim 1 wherein said collection of a fraction with a molecular weight equal up or greater than 14,000 daltons is performed by ultrafiltration.

4. The method for preparing a bioactive glycoprotein fraction as recited in claim 1 wherein said collection of a fraction with a molecular weight equal up or greater than 14,000 daltons is performed by centrifugal filtration.

5. The method for preparing a bioactive glycoprotein fraction containing a glycoprotein as a main component as recited in claim 1 wherein said hot water extraction is performed at 1:2 atmosphere pressure.

6. The method for preparing a bioactive glycoprotein fraction containing a glycoprotein as a main component as recited in claim 1 wherein said removing of resulting precipitate and floating matter is performed at 4° C.

7. The method for preparing a bioactive glycoprotein fraction containing a glycoprotein as a main component as recited in claim 1 wherein said removing of resulting precipitate and floating matter is performed by centrifugation.

8. The method for preparing a bioactive glycoprotein fraction containing a glycoprotein as a main component as recited in claim 1 wherein said removing of resulting precipitate and floating matter is performed by skimming.

9. The method for preparing a bioactive glycoprotein fraction containing a glycoprotein as a main component as recited in claim 1 wherein said removing of resulting precipitate and floating matter is performed by pipetting.

10. The method for preparing a bioactive glycoprotein fraction as recited in claim 1 further comprising purifying said above fraction to obtain the glycoprotein fraction with average molecular weight of 20,000 daltons.

11. The method for preparing a bioactive glycoprotein fraction as recited in claim 10 wherein said purification is performed using gel filtration chromatography.

12. The method for preparing a bioactive glycoprotein fraction as recited in claim 10 wherein said purification is performed using electrophoresis.

13. A bioactive glycoprotein fraction produced by the process of claim 1.

14. An antidiabetic, antihypertensive, antiobesity and antihyperlipidemic product comprising the bioactive glycoprotein fraction of claim 13.

15. The antidiabetic, antihypertensive, antiobesity and antihyperlipidemic product recited in claim 14 further comprising vitamins.

16. The antidiabetic, antihypertensive, antiobesity and antihyperlipidemic product recited in claim 14 further comprising minerals.

17. The antidiabetic, antihypertensive, antiobesity and antihyperlipidemic product recited in claim 14 further comprising vitamins and minerals.

18. The antidiabetic, antihypertensive, antiobesity and antihyperlipidemic product recited in claim 14 further comprising herbs, mushrooms, and other nutritional ingredients.

19. The antidiabetic, antihypertensive, antiobesity and antihyperlipidemic product recited in claim 14 wherein said product may be in the form of a tablet.

20. The antidiabetic, antihypertensive, antiobesity and antihyperlipidemic product recited in claim 14 wherein said product may be in the form of a capsule.

21. The antidiabetic, antihypertensive, antiobesity and antihyperlipidemic product recited in claim 14 wherein said product may be in the form of a granule.

22. The antidiabetic, antihypertensive, antiobesity and antihyperlipidemic product recited in claim 14 wherein said product may be in the form of a liquid, including tincture and drink.

23. A health food having one or more of the properties from the group consisting of antidiabetic, antihypertensive, antiobesity and antihyperlipidemic activities wherein said health food comprises the bioactive glycoprotein fraction of claim 14 is used as a food additive.

24. A food product having one or more of the properties from the group consisting of antidiabetic, antihypertensive, antiobesity and antihyperlipidemic activities wherein said food product comprises the bioactive glycoprotein fraction of claim 14 is used as a food additive.

25. A bioactive glycoprotein fraction produced by the process of claim 1 wherein said bioactive glycoprotein fraction possesses an average molecular weight of about 20,000 daltons.

26. A health food or food product comprising at least one antidiabetic, antihypertensive, antiobesity and antihyperlipidemic activities wherein said bioactive glycoprotein fraction of claim 25 is used as a food additive.

27. An antidiabetic, antihypertensive, antiobesity and antihyperlipidemic product comprising the bioactive glycoprotein fraction of claim 25.

28. The antidiabetic, antihypertensive, antiobesity and antihyperlipidemic product recited in claim 27 further comprising vitamins.

29. The antidiabetic, antihypertensive, antiobesity and antihyperlipidemic product recited in claim 27 further comprising minerals.

30. The antidiabetic, antihypertensive, antiobesity and antihyperlipidemic product recited in claim 27 further comprising vitamins and minerals.

31. The antidiabetic, antihypertensive, antiobesity and antihyperlipidemic product recited in claim 27 further comprising herbs, mushrooms, and other nutritional ingredients.

32. The antidiabetic, antihypertensive, antiobesity and antihyperlipidemic product recited in claim 27 wherein said product may be in the form of a tablet.

33. The antidiabetic, antihypertensive, antiobesity and antihyperlipidemic product recited in claim 27 wherein said product may be in the form of a capsule.

34. The antidiabetic, antihypertensive, antiobesity and antihyperlipidemic product recited in claim 27 wherein said product may be in the form of a granule.

35. The antidiabetic, antihypertensive, antiobesity and antihyperlipidemic product recited in claim 27 wherein said product may be in the form of a liquid, including tincture and drink.

36. A health food having one or more of the properties from the group consisting of antidiabetic, antihypertensive, antiobesity and antihyperlipidemic activities wherein said health food comprises the bioactive glycoprotein fraction of claim 27.

37. A food product having one or more of the properties from the group consisting of antidiabetic, antihypertensive, antiobesity and antihyperlipidemic activities wherein said food product comprises the bioactive glycoprotein fraction of claim 27.

* * * * *